United States Patent [19]

Di Giorgio et al.

[11] Patent Number: Plant 7,124

[45] Date of Patent: Jan. 23, 1990

[54] CARNATION NAMED CHANTAL

[75] Inventors: Antonio Di Giorgio; Renato Di Giorgio, both of San Remo, Italy

[73] Assignee: Laboratoire de Physiologie Vegetale, La Londe-Les Maures, France

[21] Appl. No.: 294,519

[22] Filed: Dec. 21, 1988

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new and distinct variety of standard carnation plant distinguished particularly by its very large blooms of a Venetian Pink coloration which are produced profusely during the Spring, Midseason and Fall flowering seasons on a plant having a recurrent blooming habit, the flowers being borne singly on long, strong, upright stems of a plant reaching a height of about 130 cm. at eight months of growth and having moderately abundant foliage.

1 Drawing Sheet

BACKGROUND OF THE NEW PLANT

This new carnation variety originated as a seedling of a hybrid developed by us in 1983 at our nursery at San Remo, Italy, by crossing two varieties selected from our collection of carnations maintained at our nursery for breeding purposes. This particular seedling was selected for propagation because of its very pleasing Venetian Pink Flowers produced on long, strong, upright stems of a tall plant having excellent characteristics for commercial propagation for cut flower production. This selected seedling was propagated by us by means of cuttings at our nursery in Sam Remo with such satisfactory results that we directed continued propagation of this new plant at our San Remo nursery through several successive generations by cuttings, which proved to us that the novel characteristics of the selected seedling would be retained from generation to generation and its homogeneity could be assured.

Our new carnation variety is now being propagated for commercial purposes by means of cuttings, as well as in-vitro propagation procedures, at Etablissements Barberet et Blanc, Laboratoire de Physiologie Vegetable, at 83250 La Londe-Les Maures, France.

DESCRIPTION OF THE DRAWING

Our new standard carnation variety is illustrated by the accompanying photographic drawing, which shows several blooming stems with flowers in several stages of development, together with a single stem having a bud at a stage just prior to dividing of the sepals for opening of the full blossom, the color rendition, being as nearly true to that herein specified as is reasonably possible to obtain by professional photographic procedures.

DESCRIPTION OF NEW PLANT

The following is a detailed description of our new carnation variety based upon observation of plants grown in greenhouse, as well as outside, at San Remo, Italy, and at La Londe-Les Maures, France. The color designations stated herein are according to The R.H.S. Colour Chart published by The Royal Horticultural Society of London, England.

THE PLANT

Origin: Seedling.

Parentage:

*Seed parent.*—Variety No. 845.

*Pollen parent.*—Variety No. 291. Both parents are unpatented and are identified in our breeding records maintained in our nursery office at Via Villetta 41, 18038 San Remo, Italy.

Classification:

*Botanic.*—Dianthus Caryophyllus. p2 *Commercial*.—Standard Carnation.

Form: An erect bush having at least four stems emitted near the ground.

Height: Averages about 130 cm. at eight months of growth.

Main stem length: Less than 15 cm. due to pinching.

Branching: This plant provides normal branching.

Growth: Vigorous, upright and rigid.

Foliage:

*Quantity.*—Moderately abundant.

*Number of leaves.*—More than 120.

*Leaf size.*—(At the seventh node.) Averages about 13.1 cm. long and about 0.85 cm. wide.

*Leaf shape.*—Oblong with upwardly rolled margins.

*Texture.*—Leathery.

*Color.*—Both upper side and under side, 139-A.

*Ribs and veins.*—Hardly noticeable.

*Rachis.*—Hardly noticeable.

*Leaflets.*—None.

THE BUD

Size: Large.

*Diameter.*—Averages about 2.3 cm.

*Length.*—Averages about 2.7 cm.

Shape: Ovoid.

Rate of opening: Normal.

Color of petals: When sepals first divide, 49-B/C. When petals begin to unfurl, 49-A/B, the same as at full bloom.

Sepals:

*Number.*—Six.

*Shape.*—Generally ovate but joined together at their lower parts and having an acuminate apex.

*Character.*—The sepals are hooded over the bud and stand up when the flower opens.

*Color.*—Inside, 149-D. Outside, 143-B/C.

*Striae.*—Longitudinal.

Calyx:
*Shape.*—Funnel-shaped and broad.
*Aspect.*—Smooth.
*Splitting.*—A little splitting sometimes occurs.
Flower stem:
*Length.*—About 78 cm., in average, cut at the tenth node.
*Character.*—Erect and rigid.
*Color.*—139-A.

THE FLOWER

Blooming habit: Recurrent. This plant blooms profusely in the Spring, Midseason and Fall blooming periods with a tendency to give few blooms in the Fall.
Size of flower: Very large.
*Diameter.*—Averages about 8.5 cm.
*Depth.*—Averages about 6 cm.
Borne: Singly on a long, strong, upright stem.
Shape: When bloom first opens, high-centered. When bloom matures, dome-shaped.
Petalage:
*Number of petals.*—Averages about eighty-seven.
*Arrangement.*—Imbricated.
*Form.*—Fan-shaped with very rounded edges and serrated at the apex.
*Texture.*—Leathery.
*Appearance.*—Satiny.
*Color.*—Both outer petals and inside petals: Body — 49-A/B. Base — Greenish white. Reverse side — 49-B/C.
*Petaloids.*—Number: Less than seven. Size: Smaller than the petals. Color: The same as the petals.

Flower stem:
*Character.*—Upright with good strength with outwardly curved foliage.
Discoloration after full bloom: Very little.
Persistence: On the plant, the flowers hang on and dry.
Fragrance: Perceptible
Lasting quality: As a cut flower, at least ten days in vase keeping.

THE REPRODUCTIVE ORGANS

Stamens:
*Number.*—Two to six.
*Arrangement.*—Around the ovary.
*Anthers.*—Size: Less than 4 mm.
Pistils:
*Number.*—Four.
*Styles.*—Length: About 1.4 cm. Color: Pink.
*Stigma.*—Color: Pink.
Character of ovaries: Ribbed.

This plant most resembles the variety 'Barlo' (unpatented) but is distinguished by having a more serrated flower petal and a very much less likelihood of splitting.

We claim:

1. The new and distinct standard carnation variety, substantially as herein shown and described, particularly characterized by the very large size of its Venetian Pink colored flowers and the produce production of flowers on strong, upright stems having moderately abundant foliage during the recurrent flowering periods of the plant.

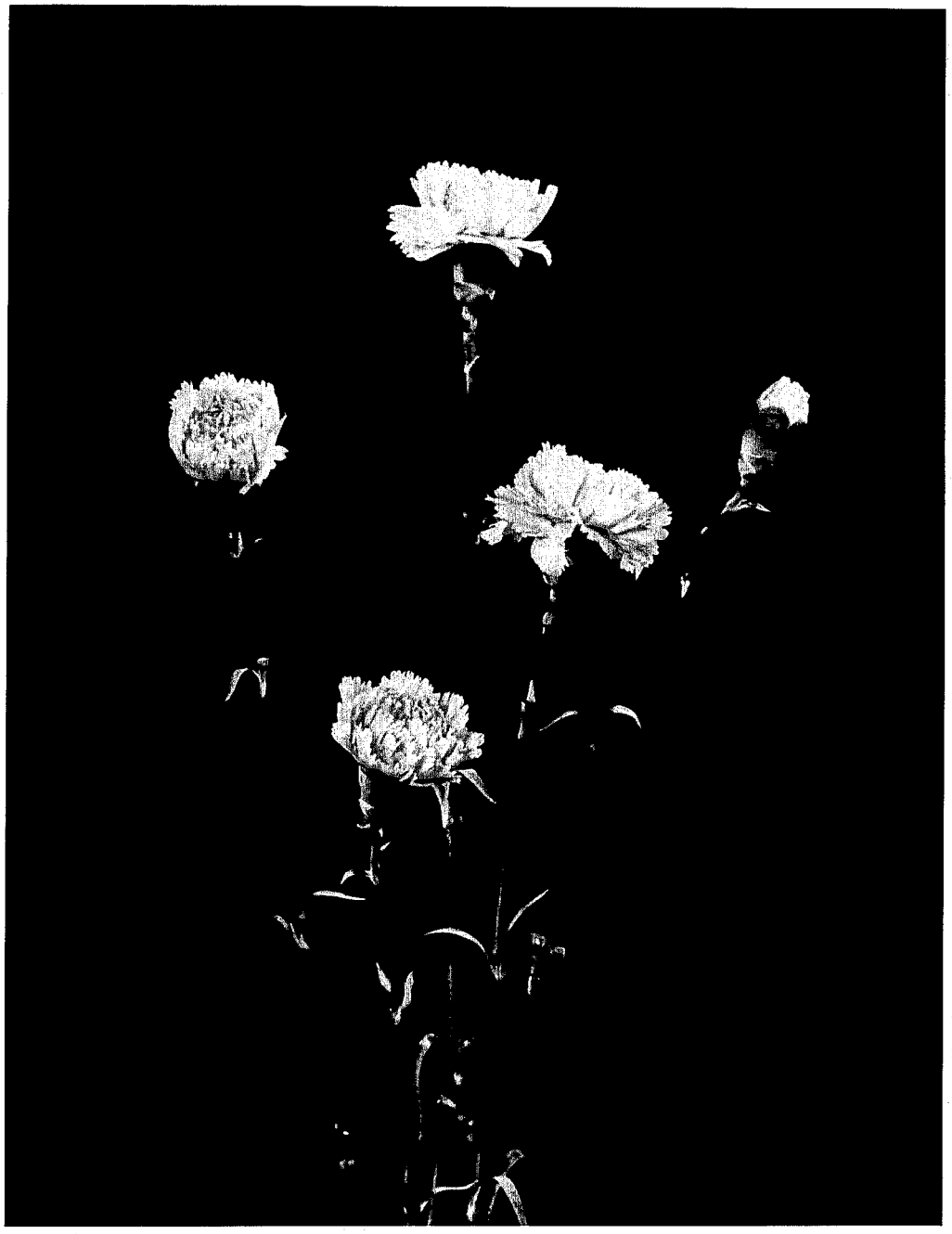

* * * * *